United States Patent
Lin et al.

(10) Patent No.: US 12,185,988 B2
(45) Date of Patent: Jan. 7, 2025

(54) INTERSPINOUS PROCESS DEVICE AND DEVICE FOR STABILIZING THEREOF

(71) Applicant: BAUI Biotech Co., Ltd., New Taipei (TW)

(72) Inventors: Yu-Sheng Lin, New Taipei (TW); Kuo-Wei Tseng, New Taipei (TW); Chiung-Chyi Shen, Taichung (TW); Meng-Yin Yang, Taichung (TW)

(73) Assignee: BAUI Biotech Co., Ltd., New Taipei (TW)

( * ) Notice: Subject to any disclaimer, the term of this patent is extended or adjusted under 35 U.S.C. 154(b) by 0 days.

(21) Appl. No.: 17/834,398

(22) Filed: Jun. 7, 2022

(65) Prior Publication Data
US 2023/0270474 A1 Aug. 31, 2023

(30) Foreign Application Priority Data
Feb. 25, 2022 (TW) .................................. 111106993

(51) Int. Cl.
*A61B 17/70* (2006.01)

(52) U.S. Cl.
CPC ...... *A61B 17/7067* (2013.01); *A61B 17/7065* (2013.01); *A61B 17/7068* (2013.01)

(58) Field of Classification Search
CPC ............ A61B 17/7065; A61B 17/7067; A61B 17/7068; A61B 17/7062; A61F 2/4405; A61F 2/4455–447; A61F 2250/0004–0009; A61F 2250/0048
See application file for complete search history.

(56) References Cited

U.S. PATENT DOCUMENTS

| | | | | |
|---|---|---|---|---|
| 2004/0086325 | A1* | 5/2004 | Friesen | F16C 11/02 403/150 |
| 2005/0203512 | A1* | 9/2005 | Hawkins | A61B 17/7062 606/279 |
| 2007/0100340 | A1* | 5/2007 | Lange | A61B 17/7065 606/279 |
| 2007/0167945 | A1* | 7/2007 | Lange | A61B 17/7062 623/17.13 |
| 2008/0071378 | A1* | 3/2008 | Zucherman | A61B 17/7068 606/90 |
| 2008/0195152 | A1* | 8/2008 | Altarac | A61B 17/7065 623/17.11 |

(Continued)

FOREIGN PATENT DOCUMENTS

| | | |
|---|---|---|
| CN | 102341066 B | 7/2014 |
| CN | 114052873 A | 2/2022 |

*Primary Examiner* — Julianna N Harvey
*Assistant Examiner* — Anna V. Little
(74) *Attorney, Agent, or Firm* — ScienBiziP, P.C.

(57) ABSTRACT

The present disclosure provides an interspinous process device. The interspinous process device may include a main body having a cavity formed therein, the main body being configured to be disposed between the two adjacent spinous processes; and a spacer configured to be arranged in the cavity of the main body. When the main body is disposed between the two adjacent spinous processes and the spacer is arranged in the cavity of the main body, a volume of the cavity may be greater than a volume of the spacer, a height of the cavity may be equal to a height of the spacer, and a width of the cavity may be greater than a width of the spacer.

9 Claims, 6 Drawing Sheets

(56) References Cited

U.S. PATENT DOCUMENTS

| | | | | |
|---|---|---|---|---|
| 2010/0076560 A1* | 3/2010 | Weng | A61B 17/7062 | |
| | | | 606/86 R | |
| 2010/0106190 A1* | 4/2010 | Linares | A61B 17/7067 | |
| | | | 606/249 | |
| 2010/0249840 A1* | 9/2010 | Tanaka | A61B 17/7062 | |
| | | | 606/249 | |
| 2011/0029020 A1* | 2/2011 | Gordon | A61B 17/7062 | |
| | | | 606/248 | |
| 2011/0313457 A1* | 12/2011 | Reglos | A61B 17/7068 | |
| | | | 606/279 | |
| 2012/0089184 A1* | 4/2012 | Yeh | A61B 17/7068 | |
| | | | 606/248 | |
| 2012/0089185 A1* | 4/2012 | Gabelberger | A61F 2/4405 | |
| | | | 606/249 | |
| 2012/0215232 A1* | 8/2012 | Olsen | A61B 17/8888 | |
| | | | 606/139 | |
| 2012/0215261 A1* | 8/2012 | Massoudi | A61B 17/7064 | |
| | | | 606/279 | |
| 2012/0226312 A1* | 9/2012 | Thalgott | A61B 17/7067 | |
| | | | 606/279 | |
| 2013/0090692 A1* | 4/2013 | Nuckley | A61B 17/7068 | |
| | | | 606/246 | |
| 2013/0158604 A1* | 6/2013 | Okamoto | A61B 17/7065 | |
| | | | 606/249 | |
| 2013/0253585 A1* | 9/2013 | Garcia | A61B 17/7068 | |
| | | | 606/279 | |
| 2013/0296940 A1* | 11/2013 | Northcutt | A61B 17/7068 | |
| | | | 606/249 | |
| 2014/0018924 A1* | 1/2014 | McManus | A61F 2/4455 | |
| | | | 623/17.16 | |
| 2014/0114355 A1* | 4/2014 | Robinson | A61B 17/88 | |
| | | | 606/279 | |
| 2014/0228886 A1* | 8/2014 | Aflatoon | A61B 17/7065 | |
| | | | 606/249 | |
| 2014/0243898 A1* | 8/2014 | Fessler | A61B 17/7071 | |
| | | | 606/249 | |
| 2016/0220285 A1* | 8/2016 | Fortin | A61F 2/4405 | |
| 2016/0374733 A1* | 12/2016 | Fessler | A61B 17/7068 | |
| | | | 606/279 | |
| 2017/0027619 A1* | 2/2017 | Ganter | A61B 17/7065 | |
| 2017/0181773 A1* | 6/2017 | Gustine | A61B 17/7068 | |
| 2017/0252073 A1* | 9/2017 | Salvermoser | A61B 90/92 | |

* cited by examiner

INTERSPINOUS PROCESS DEVICE AND DEVICE FOR STABILIZING THEREOF

CROSS-REFERENCE TO RELATED APPLICATION(S)

This application claims the benefit of and priority to Taiwan Patent Application No. 111106993, filed on Feb. 25, 2022, the contents of which are hereby incorporated by reference herein in their entirety.

BACKGROUND

1. Field

The present disclosure generally relates to medical devices and, more particularly, to interspinous process devices.

2. Related Art

Intervertebral disease, an abnormality of the intervertebral joints and the associated tissues surrounding the spine, is often accompanied by severe pain. For example, a patient having subluxation or a herniated intervertebral disc may suffer from severe pain. Typically, a patient with severe pain may only relieve the pain by surgery.

An interspinous process device is a medical device used by a physician during surgery. The interspinous process device is a spinal implant that can retain movement. The interspinous process device is able to separate adjacent spinous processes to relieve the pain of patient.

Conventional interspinous process devices typically provide poor support and stability. Thus, displacement of an interspinous process device often occurs in vertebrae. As a result, a conventional interspinous process device cannot be fixed between adjacent spinous processes effectively, often resulting in the changing of the segment of the vertebrae after surgery. Furthermore, conventional interspinous process devices cannot be adjusted in accordance with the size of the space between the spinous processes, so manufacturers typically produce devices of different sizes to adapt different individuals.

Accordingly, there is a need to provide an improved and efficient interspinous process device to solve at least the above-mentioned problems.

BRIEF SUMMARY OF THE DISCLOSURE

The present disclosure provides an interspinous process device disposed between two adjacent spinous process by distracting a narrow gap of spinous process in advance, so as to achieve the purpose of distracting and fixing the spinous process to achieve the purpose of alleviating the symptoms of patient.

In a first aspect of the present disclosure, an interspinous process device for maintaining a separation distance between two adjacent spinous processes in a spine may be provided. The interspinous process device may include: a main body having a cavity formed therein, the main body being configured to be disposed between the two adjacent spinous processes in the spine; and a spacer configured to be arranged in the cavity of the main body. When the main body may be disposed between the two adjacent spinous processes and the spacer may be arranged in the cavity of the main body, a volume of the cavity may be greater than a volume of the spacer, a height of the cavity may be equal to a height of the spacer, and a width of the cavity may be greater than a width of the spacer.

In some embodiments of the first aspect, the main body may include a lid and a base, and the lid may include an interconnect member configured to engage the base to facilitate adjustment of the separation distance between the two adjacent spinous processes in a direction of a longitudinal axis along the spine.

In some embodiments of the first aspect, at least one of the lid and the base may define an orienting slot arranged thereon to establish an orientation reference for the spacer, and the spacer may include an engaging portion that is structurally complementary to the orienting slot of the main body to maintain a position of the spacer within the cavity.

In some embodiments of the first aspect, the engaging portion may include a barb.

In some embodiments of the first aspect, the each of the lid and the base may include a spinous process contact portion that is structurally complementary to a spinous process. The spinous process contact portion may be configured to contact the two adjacent spinous processes to maintain a position of the main body between the two adjacent spinous processes.

In some embodiments of the first aspect, each of the main body, the spacer and the spinous process contact portion may include one or more of metal, plastic, or silicone.

In some embodiments of the first aspect, the spacer may include a tool orienting slot.

In some embodiments of the first aspect, a ratio of the width of the spacer to the width of the cavity may range from 1:4 to 1:2.

In a second aspect of the present disclosure, stabilizing device for fixing the interspinous process device may be provided. The stabilizing device may include a pair of wing structures. Each wing structure may be configured to extend along a longitudinal axis of the spine. Each of the pair of wing structure may include a main body engaging portion and an end portion. The main body engaging portion may be located in a middle region of the wing structure, and the main body engaging portion may be configured to engage the main body. The end portion may be configured to abut against one of the two adjacent spinous processes.

In some embodiments of the second aspect, the stabilizing device may further include a fastener configured to be installed in the main body engaging portion to fasten the main body and the stabilizing device together.

In some embodiments of the second aspect, the fastener may include at least two sub-fasteners that are structurally separable.

In some embodiments of the second aspect, the end portion may include a plurality of spikes.

In some embodiments of the second aspect, the spikes in the plurality of spikes may be arranged to form a staggered pattern.

In some embodiments of the second aspect, a length of at least one of the plurality of spikes may range from 0.5 mm to 22 mm.

In some embodiments of the second aspect, the wing structure may include a groove to provide flexibility for the stabilizing device.

In some embodiments of the second aspect, the wing structure may include one or more of metal, plastic, or silicone.

In some embodiments of the second aspect, a length of the wing structure may range from 2 cm to 20 cm.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

In accordance with common practice, the various described features are not drawn to scale and are drawn to emphasize features relevant to the present disclosure. Like reference characters denote like elements throughout the figures and text.

DETAILED DESCRIPTION

Figure 1:
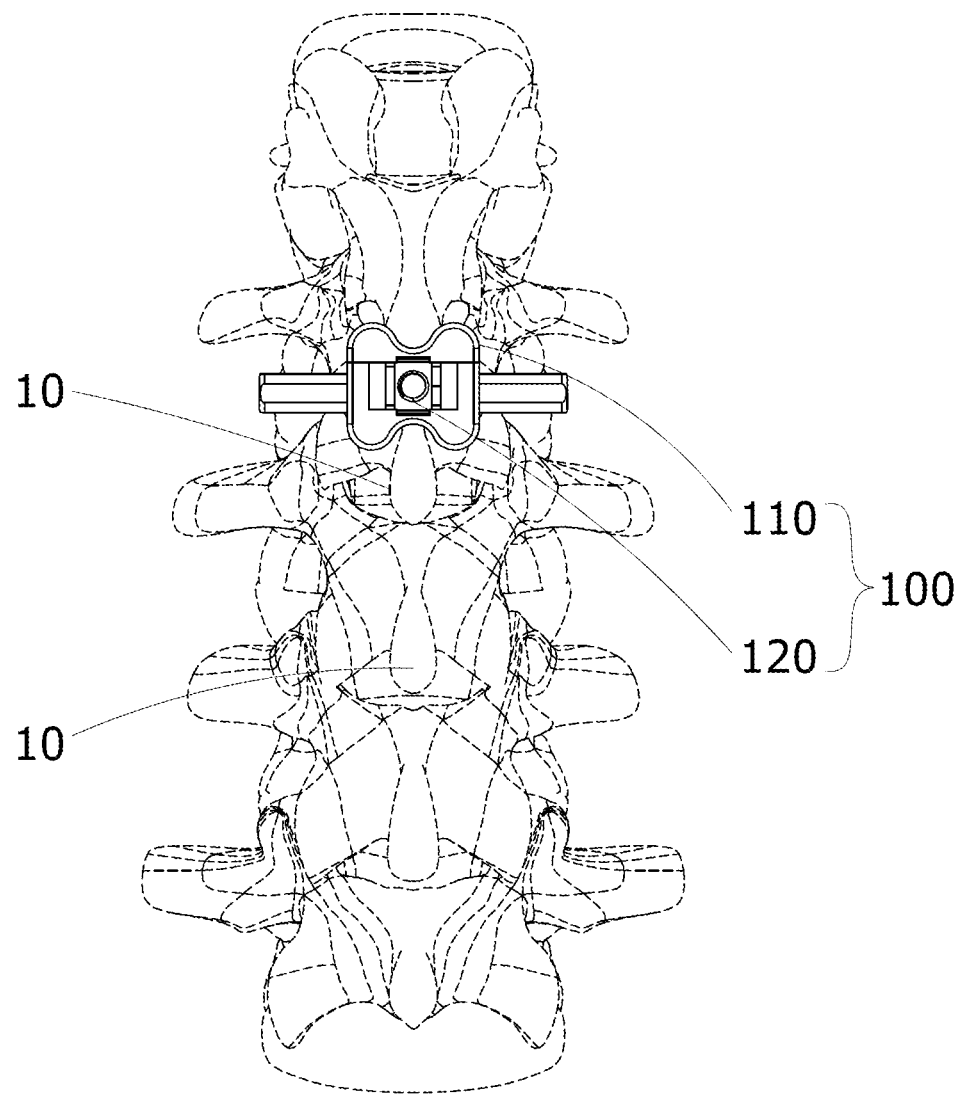
FIG. 1 is a front view of an interspinous process device showing the interspinous process device applied to a spine in view of backside of a human body, according to an embodiment of the present disclosure.

The present disclosure will now be described more fully hereinafter with reference to the accompanying drawings, in which exemplary embodiments of the disclosure are shown. This disclosure may, however, be embodied in many different forms and should not be construed as limited to the exemplary embodiments set forth herein. Rather, these exemplary embodiments are provided so that this disclosure will be thorough and complete, and will fully convey the scope of the disclosure to those skilled in the art. Like reference numerals refer to like elements throughout.

The terminology used herein is for the purpose of describing particular exemplary embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," or "includes" and/or "including" or "has" and/or "having", when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The term "longitudinal axis" described herein refers to the direction along the spine (e.g., the "y-axis" in the figures) when the interspinous process device of the present disclosure is disposed between two adjacent spinous processes. The "horizontal axis" described herein is the direction perpendicular to the longitudinal axis and extends to the left and right sides of the human body (e.g., the "x-axis" in the figures) when the interspinous process device of the present disclosure is disposed between two adjacent spinous processes. The "front-rear axis" described herein is perpendicular to the longitudinal axis and horizontal axis (e.g., the "z-axis" in the figures).

The interspinous process device of the present disclosure is disposed between two adjacent spinous process by distracting a narrow gap of spinous process in advance, so as to achieve the purpose of distracting and fixing the spinous process to achieve the purpose of alleviating the symptoms of patient.

FIG. 1 is a front view of an interspinous process device showing the interspinous process device applied to a spine in view of backside of a human body, according to an embodiment of the present disclosure. As shown in FIG. 1, the interspinous process device 100 of the present disclosure is disposed between two adjacent spinous processes 10. The interspinous process device 100 of the present disclosure includes a main body 110 and a spacer 120 arranged on the main body 110. The main body 110 of the present disclosure is adjustable, which enables an operator (such as a surgeon or other medical personnel) to adjust the main body 110 to be suitable for various spinal regions (such as the cervical spine, lumbar spine, or thoracolumbar spine) or variable interspinous process spacing of various individuals (e.g., adults or children) with a single main body. After adjusting the main body 110 to fit the distance between the spinous processes 10 and disposing the main body 110 between the adjacent spinous processes 10, the operator then may dispose the spacer 120 in the main body 110. The spacer 120 is substantially cuboid and arranged in the main body 110 to provide longitudinal support, thus causing the main body 110 to maintain a predetermined distance between the spinous processes 10 to prevent narrowing of the distance between the spinous processes 10.

Figure 2A:
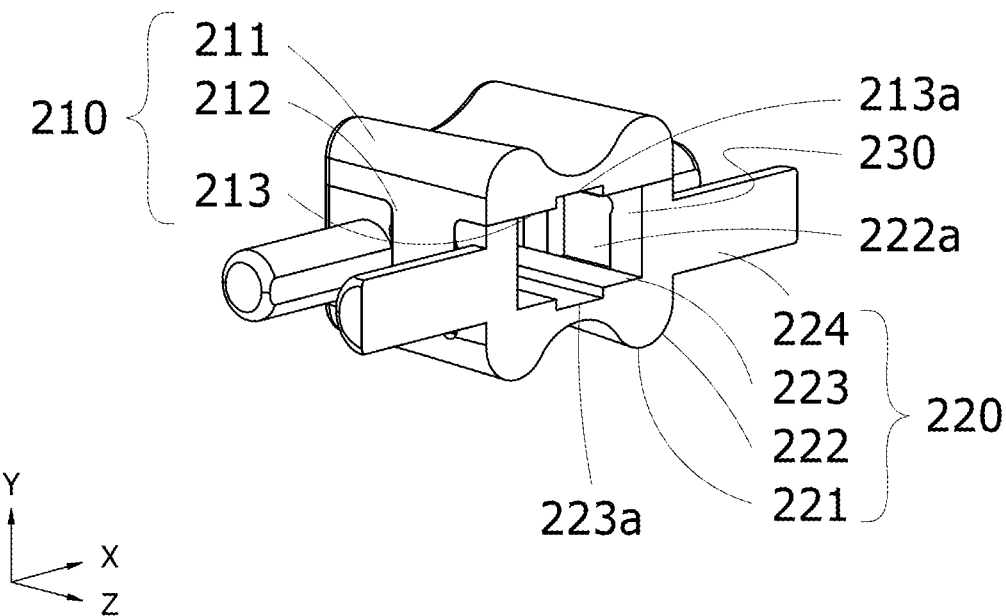
FIGS. 2A and 2B are cross-sectional views of the main body of the interspinous process device, according to an embodiment of the present disclosure.
Figure 2B:
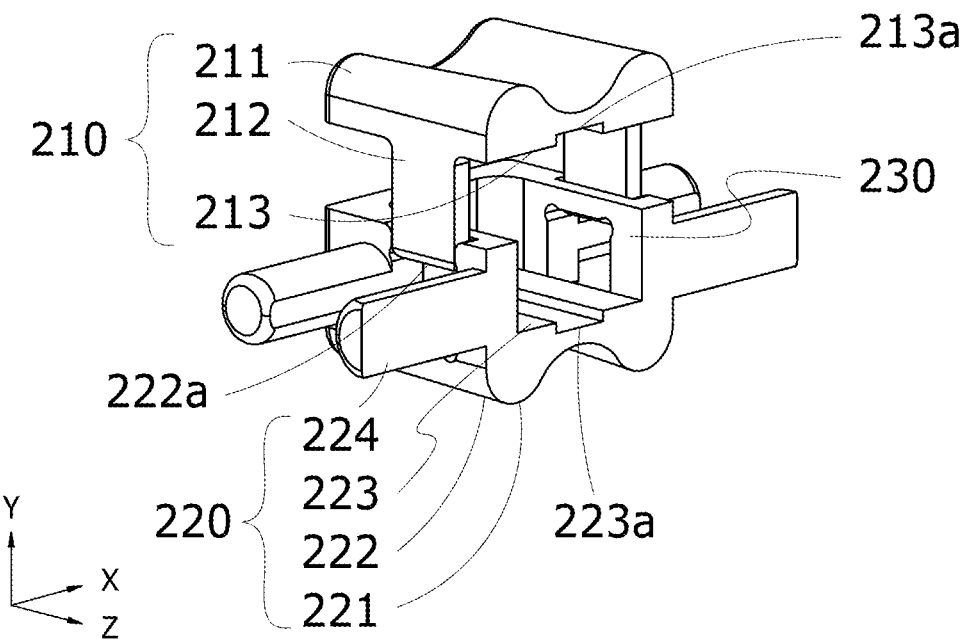

FIGS. 2A and 2B are cross-sectional views of the main body 110 of the interspinous process device 100, according to an embodiment of the present disclosure. The main body 110 has a cavity 230 formed therein. The main body 110 is configured to be disposed between the two adjacent spinous processes. The main body 110 is formed by a lid 210 and a base 220 along a longitudinal axis (the y-axis in FIGS. 2A and 2B). The main body 110 is mainly composed of a medical material that can withstand a certain external force, and the medical material has a certain strength to provide an appropriate supporting force for the main body 110. For example, the medical material may be a metallic material, a plastic material, a silicone material, or a combination of any two or more of the above. In some embodiments, the metallic material may include titanium, stainless steel, nitinol, or tantalum. In some embodiments, the plastic material may include polyetheretherketone (PEEK). In some embodiments, the silicone material may include silicone.

Each of the lid 210 and the base 220 of the main body 110 has a spinous process contact portion 211/221 configured to be in contact with the spinous process 10. The spinous process contact portion 211/221 is structurally complementary to the spinous process 10 such that an area of the main body 110 that contacts the spinous process 10 is increased. As such, the stability of the interspinous process device 100 is enhanced accordingly. For example, as shown in FIG. 2A, a middle area of the spinous process contact portion 211/221 may be recessed inward to correspond to the protruding spinous processes 10, thereby fixing the main body 110 between the spinous processes 10). In some embodiments, a material of the spinous process contact portion 211/221 may be made of the same medical material as that of the remainder of main body 110. For example, metallic materials may be used in both the remainder of main body 110 and spinous process contact portion 211/221. In other embodiments, different medical materials may be used in the spinous process contact portion 211/221 and the remainder of main body 110. For example, the remainder of main body 110 may be made of a metallic material, while the spinous process contact portion 211/221 may be made of a composite material including metal and silicone to increase comfort of the patient.

The lid 210 and the base 220 may be connected through an interconnection member 212 provided on the lid 210 to achieve a simple and adjustable connection. For example, as can be seen from the embodiment shown in FIGS. 2A and 2B, the side surface of the lid 210 may have interconnect members 212 extending from the spinous process contact portion 211 to the base 220, and side walls 222 of the base 220 may be provided with a space for receiving interconnecting members 212, such as receiving slot 222a. The interconnect member 212 may be configured to movably connect the lid 210 with the base 220, thereby forming the main body 110 with a cavity 230 that is adjustable in height.

For example, in the embodiment shown in FIG. 2A, the interconnect member 212 of the lid 210 may be fully engaged with the receiving slot 222a of the base 220, thereby forming the main body 110 that is suitable for a smaller separation distance between two adjacent spinous processes 10. In some embodiments, as shown in FIG. 2B, the interconnect member 212 of the lid 210 may be partially engaged with the receiving slot 222a of the base 220, so that the lid 210 and the base 220 are able to facilitate a longer separation distance in the longitudinal direction (e.g., via the spacer 120), so as to render the main body 110 suitable for a larger separation distance between two adjacent spinous processes 10. In other embodiments, the interconnect member 212 may be provided with a length adjustment mechanism (not shown) that can adjust a distance in the longitudinal direction to achieve adjustability of the main body 110.

In some embodiments, as shown in FIGS. 2A and 2B, each side surface of the lid 210 is provided with one interconnect member 212. However, in other embodiments, as shown in FIG. 5B, each side surface of the lid 210 may be provided with a plurality of interconnect members 212.

Each of the lid 210 and the base 220 may have an inner surface 213/223 which is opposite to the spinous process contact portion 211/221. The inner surface 213/223 is in contact with the spacer 120 and is provided with an orienting slot 213a/223a to establish an orienting reference for the spacer 213/223, thereby maintaining a position of the spacer 120 within the main body 110. In some embodiments, the orienting slot 213a/223a may be designed to be rectangular, extending parallel to the front-rear direction (the Z axis in FIG. 2) to facilitate the insertion of the spacer 120 to the main body 110.

Additionally, in some embodiments, the base 220 may be provided with a fixing member (such as fixing member 224 in FIGS. 2A and 2B) for engaging a stabilizing device (described below in conjunction with FIGS. 5A and 5B), thereby increasing the stability of the interspinous process device 100.

Figure 3:
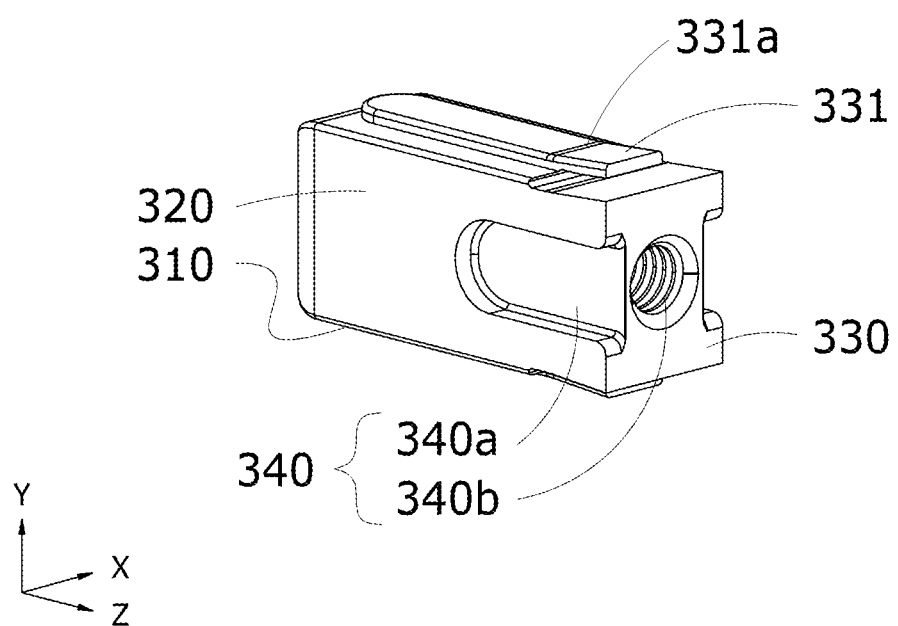
FIG. 3 is a perspective view of the spacer of the interspinous process device, according to an embodiment of the present disclosure.

FIG. 3 is a perspective view of the spacer 120 of the interspinous process device 100, according to an embodiment of the present disclosure. During surgery, the spacer 120 may be disposed in the cavity 230 of the main body 110 to provide a supporting force to the interspinous process device 100. The spacer 120 may be made of a medical material. The medical material may be a metallic material, a plastic material, a silicone material, or a combination of any two or more of the above. In some embodiments, the metallic material may include titanium, stainless steel, nitinol, or tantalum. In some embodiments, the plastic material may include polyetheretherketone (PEEK). In some embodiments, the silicone material may include silicone. In some embodiments, the spacer 120 may be made of a medical material that is identical to that of the main body 110. For example, both the spacer 120 and the main body 110 may be made of metallic material. However, in other embodiments, the main body 110 and the spacer 120 may be made of different medical materials. For example, the main body 110 may be made of composite material including metal and plastic, and the spacer 120 may be made of metallic material.

The spacer 120 may have a contact surface 310 in contact with the lid 210 of the main body 110 and the base 220, a side surface 320 not in contact with the main body 110, and a top surface 330. The contact surface 310 of the spacer 120 may be provided with an engaging portion 331 configured to engage with the orienting slot 213a/223a of the lid 210 and the base 220 of the main body 110. In some embodiments, the engaging portion 331 may be further provided with a barb 331a to abut against the inner surface 213/223 of the lid 210 and the base 220 of the main body 110 when the engaging portion 331 is fully engaged with the orienting slot 213a/223a of the lid 210 and the base 220 of the main body 110 to provide resistance when the spacer 120 is urged away from the main body 110, thereby preventing the spacer 120 from sliding out of the main body 110, such that the spacer 120 is fixed in the main body 110.

The spacer 120 may be provided with a tool orienting slot 340 to provide a working area for a tool to clamp or retain the spacer 120. In some embodiments, as shown in FIG. 3, the tool orienting slot 340 may be a groove 340a arranged on the side surface 320 of the spacer 120 to facilitate the use of a tool (e.g., forceps or tweezers) to clamp the spacer 120 into the main body 110. Also, if the spacer 120 is replaced, it may be beneficial to retract the spacer 120 from the main body 110 through the use of a tool to clamp a tool orienting slot 340 (the groove 340a indicated in FIG. 3) of the spacer 120. In another embodiment, the tool orienting slot 340 may be a screw hole 340b disposed on the top surface 330 of the spacer 120, and a tool (e.g., a screw) corresponding to the screw hole 340b may be screwed into the spacer 120 before the spacer 120 is disposed in the main body 110, so that the screw may serve as a handle for the spacer 120. The screw may be removed after the spacer 120 completely enters the main body 110. Although in the embodiment shown in FIG. 3, the spacer 120 has both the tool orienting slots 340a and 340b, in other embodiments, the tool orienting slots 340a and 340b may be selectively arranged.

Figure 4:
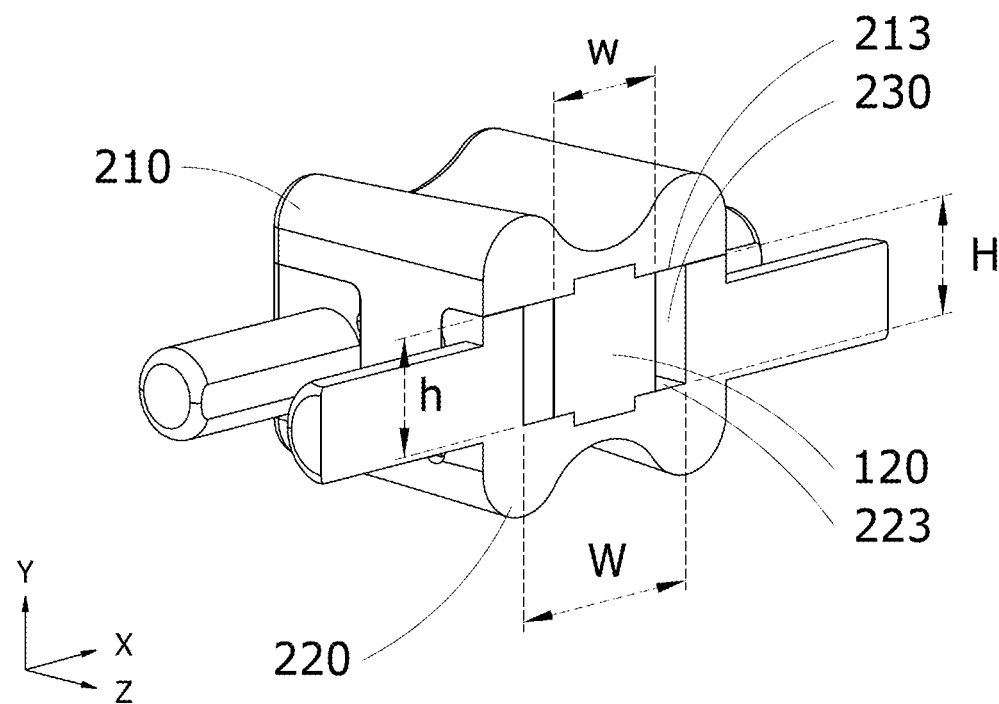
FIG. 4 is a cross-sectional view of the interspinous process device showing the main body in combination with the spacer, according to an embodiment of the present disclosure.

FIG. 4 is a cross-sectional view of the interspinous process device 100 showing the main body 110 in combination with the spacer 120, according to an embodiment of the present disclosure. The inner surfaces 213/223 of the base 220 and the lid 210 of the main body 110 are in contact with the spacer 120. Specifically, the engagement between the main body 110 and the spacer 120 is achieved by the engaging portion 331 of the spacer 120 being engaged with the orienting slots 213a/223a on the inner surface 213/223 of the main body 110 such that the spacer 120 is positioned and fixed in the cavity 230 of the main body 110, thereby preventing the spacer 120 from moving within the cavity 230.

To allow the operator (such as a physician) to arrange the spacer 120 in the main body 110, the volume of the cavity 230 of the main body 110 may be greater than the volume of the spacer 120, and a height H of the cavity 230 may be substantially equal to a height h of the spacer 120 such that the contact surface 310 of the spacer 120 may contact and abut against the inner surface 213/223 of the lid 210 and the base 220 to provide a longitudinal support force for the interspinous process device 100. Moreover, a width W of the cavity 230 may be greater than a width w of the spacer 120, thereby providing a suitable space for inserting the spacer 120 or removing the spacer out of the cavity 230 by using a tool (such as tweezers or forceps). In some embodiments, the ratio of the width w of the spacer 120 to the width W of the cavity 230 may range from 1:2 to 1:4. The height of the spacer 120 may be in the range of 2 mm to 30 mm to adapt to adjustable main body 110 that applies to variable spinous process distances and interspinous process devices 100. Thus, the appropriate height of the spacer 120 may be selected to match the particular interspinous process distance involved. For example, where the interspinous process device 100 is applied to the lumbar spine, the preferred height range of the spacer 120 may range from 7 mm to 16 mm.

In some embodiments, a barb 331a may be provided on the engaging portion 331, and the barb 331a may be configured to abut against the inner face 213/223 when the engaging portion 331 is fully engaged with the orienting slot 213a/223a of the lid 210 and the base 220 of the main body 110. Advantageously, the barb 331a may provide a force to resist the spacer 120 from pulling away from the main body 110, thereby preventing the spacer 120 from sliding out of the main body 110, thus fixing the spacer 120 within the main body 110.

To increase the stability in the horizontal direction of the interspinous process device 100, the interspinous process device 100 may be provided with a stabilizing device for fixing the interspinous process device 100.

Figure 5A:
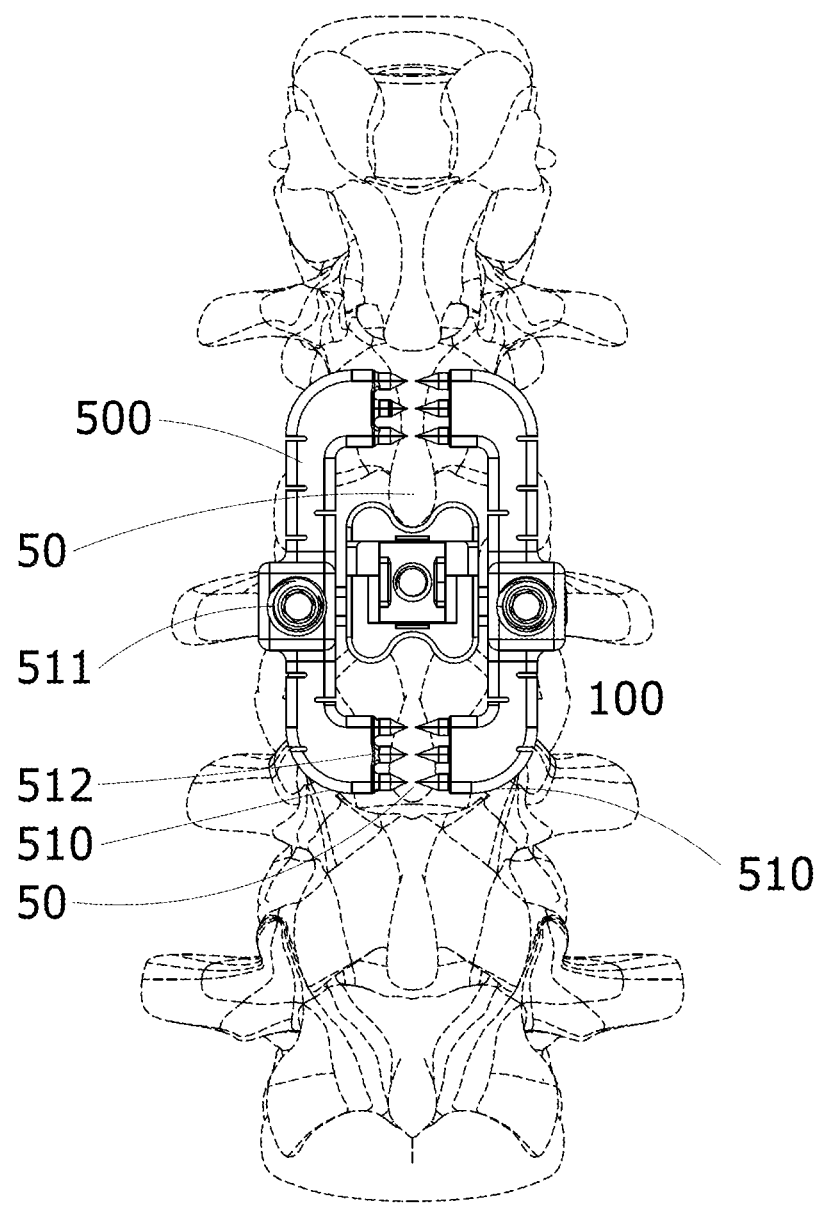
FIG. 5A is a front view of the interspinous process device in combination with a stabilizing device applied to a spine in view of backside of a human body, according to an embodiment of the present disclosure.
Figure 5B:
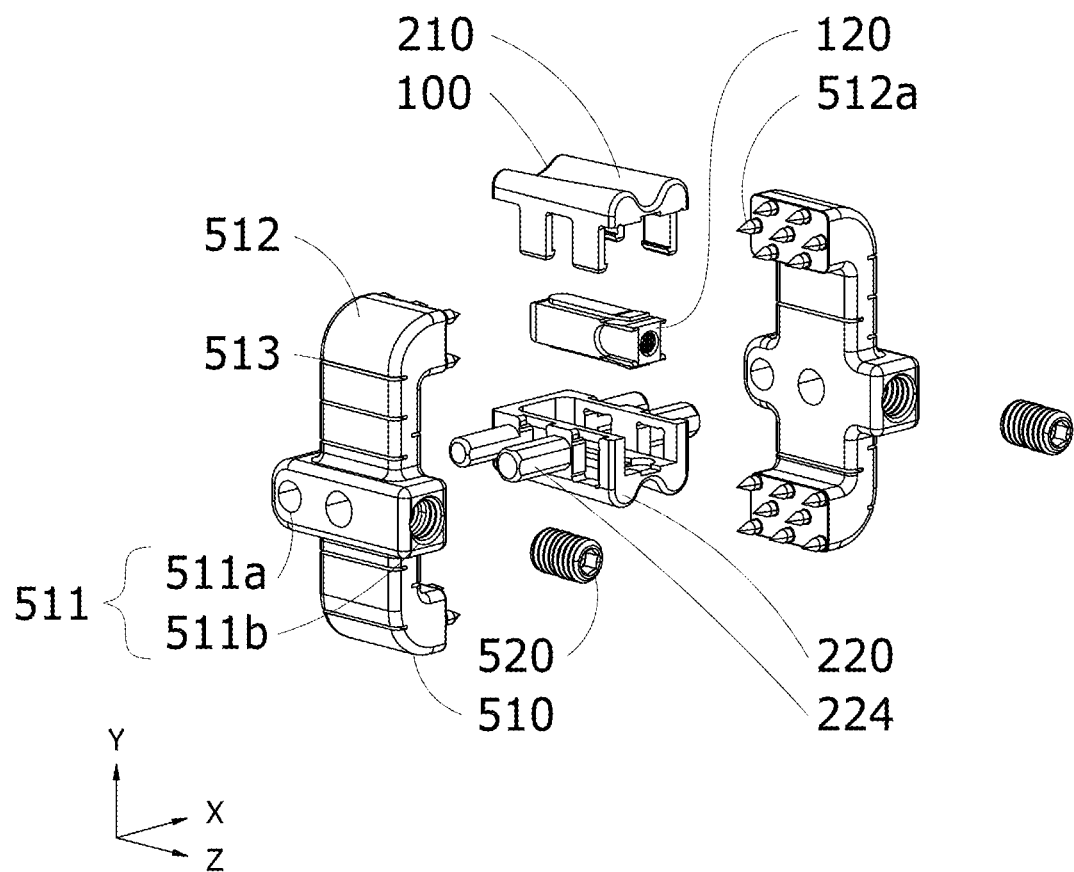
FIG. 5B is an exploded perspective view showing the interspinous process device and the stabilizing device, according to an embodiment of the present disclosure.

FIG. 5A is a front view of the interspinous process device 100, in combination with a stabilizing device 500 applied to the spine according to an embodiment of the present disclosure. As shown in FIG. 5A, the stabilizing device 500 may include a pair of symmetrical wing structures 510 disposed on the left and right sides of the interspinous process device 100. Each of the wing structures 510 may extend along the longitudinal axis and may include a main body engaging portion 511 in contact with the main body 110 of the interspinous process device 100 and two end portions 512 in contact with the spinous process 50.

Figure 5C:
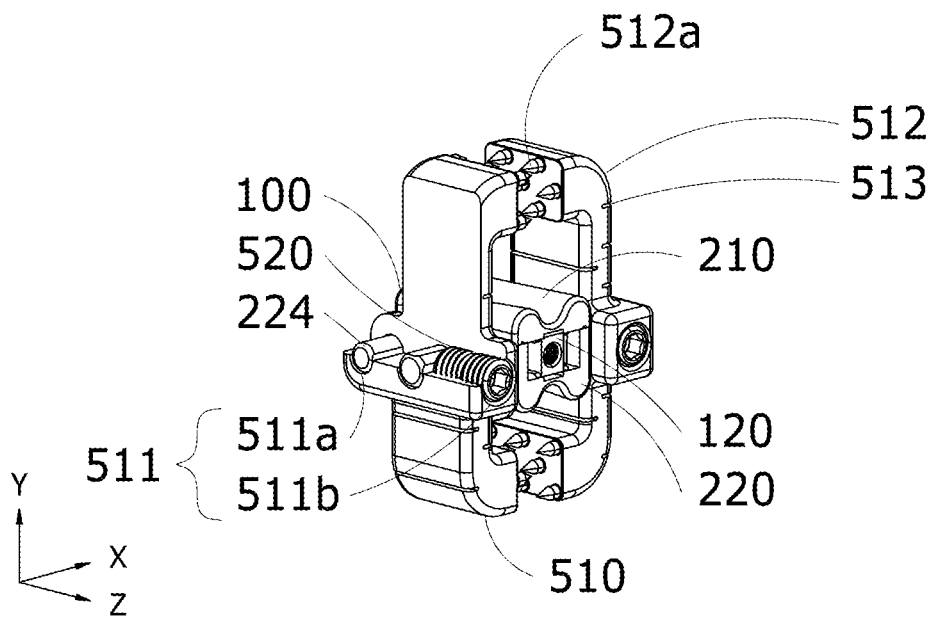
FIG. 5C is an assembled partial perspective view showing the interspinous process device and the stabilizing device, according to an embodiment of the present disclosure.

FIG. 5B is an exploded perspective view of the interspinous process device 100 in combination with the stabilizing device 500 and FIG. 5C is an assembled partial perspective view of the interspinous process device 100 in combination with the stabilizing device 500, according to an embodiment of the present disclosure. The stabilizing device 500 may be composed of a pair of symmetrical wing structures 510. The wing structures 510 may be made of medical materials. The medical materials may be metallic materials, plastic materials, silicone materials, or a combination of any two or more of the above. In some embodiments, the metallic material may include titanium metal, stainless steel, nitinol, or tantalum metal. In some embodiments, the plastic material may include polyetheretherketone (PEEK). In some embodiments, the silicone material may include silicone. The longitudinal length of the wing structure 510 may range from 2 cm to 20 cm to apply to various interspinous process devices 100. A suitable wing structure for a suitable interspinous process device 100 may be selected depending on the particular situation involved. For example, where the wing structure 510 is applied to the lumbar spine, a preferred longitudinal length of the wing structure 510 may range from 2 cm to 12 cm. A groove 513 may be provided in intervals between the main body engaging portion 511 and the end portions 512 to provide appropriate flexibility for the rigid stabilizing device 500.

The main body engaging portion 511 may be located in a middle region of the wing structure 510, and at least one through hole 511a may be formed on the main body engaging portion 511. The through hole 511a may be configured to engage with the fixing member 224 of the main body 110 so that the wing structure 510 can be arranged at the left side and right side of the interspinous process device 100 through engagement between fixing member 224 of the main body 110 and the through hole 511a of the wing structure 510. In some embodiments, the fixing member 224 may be designed to be a polygonal shape to increase the tightness of the engagement.

In some embodiments, the main body engaging portion 511 may be further provided with a fastening groove 511b (e.g., a threaded hole) substantially perpendicular to the through hole 511a. The fastening groove 511b may receive a fastener 520 (e.g., a setscrew) to fasten the main body 110 and the stabilizing device 500 together. For example, as shown in FIG. 5C, which shows a partial perspective view of the fastener 520 installed in the fastening groove 511b of the main body engaging portion 511 of the stabilizing device 500, the fixing member 224 of the main body 110 is fixed to the main body engaging portion 511 of the wing structure 510 by screwing the fastener (such as setscrew 520 in FIGS. 5A and 5B) into the fastening groove (e.g., the screw hole 511b in FIGS. 5A and 5B), thereby fastening the wing structure 510 to the left and right sides of the interspinous process device 100. In other embodiments, the fastener 520 may be composed of at least two sub-fasteners, and the sub-fasteners may be structurally separable from each other to provide tighter engagement than a single fastener.

The end portions 512 may be located at both ends in the longitudinal direction of the wing structure 510 and may be configured to abut against the spinous process 50 when the wing structure 510 is installed on the left and right sides of the interspinous process device 100 (as shown in FIG. 5A) such that the interspinous process device 100 is fixed in a space defined by two adjacent spinous processes 50 and the stabilizing device 500. Each end portion 512 of one of the pair of wing structures 510 may have a surface opposite to a surface of another end portion 512 of the other wing structure 510. The surface may have a plurality of spikes 512a arranged thereon, and the plurality of spikes 512a may not be uniform in length so as to be suitable for the non-smooth surface of the spinous process 50. In addition, the spikes 512a provided on one end portion 512 of one of the pair of wing structures 510 may be opposite the spikes 512a provided on another end portion 512 of the other wing structure 510 and may be arranged to form a staggered pattern to increase stability. In some embodiments, the length of each spike may range from 0.5 mm to 22 mm. An appropriate length of each spike may be selected, depending on the particular situation involved. For instance, a preferred length of the spike applying to the lumbar spine may range from 0.5 mm to 12 mm. In some embodiments, a diameter of the spike 512a may range from 0.1 mm to 10 mm.

In conclusion, the interspinous process device 100 of the present application may achieve adjustability of the main body to be suitable for various individuals. Furthermore, the longitudinal support force of the interspinous process device 100 of the present application may be strengthened via the spacer 120. In addition, a stabilizing device 500 may also be added to increase the horizontal stability of the interspinous process device 100.

Those skilled in the art will readily observe that numerous modifications and alterations of the device and method may be made while retaining the teachings of the disclosure. Accordingly, the above disclosure should be construed as limited only by the metes and bounds of the appended claims.

What is claimed is:

1. A medical device, comprising:
    an interspinous process device for maintaining a separation distance between two adjacent spinous processes in a spine of a human body, the interspinous process device comprising:
        a main body having a cavity formed therein, the main body being configured to be disposed between the two adjacent spinous processes in the spine of the human body, and further comprising:
            a base comprising a first spinous process contact portion, a fixing member, a side wall extending from the first spinous process contact portion, and a receiving slot formed on the side wall; and
            a lid including a second spinous process contact portion and an interconnect member extending from the second spinous process contact portion towards the base, wherein:
                the interconnect member is inserted in and moveably connected with the receiving slot in a spine direction of a longitudinal axis along the spine to form the main body and to adjust an engagement between the receiving slot and the interconnect member,
                the engagement between the receiving slot and the interconnect member is adjusted for the main body to match the separation distance between the two adjacent spinous processes by adjusting a height of the cavity, and
                the fixing member is arranged on the base along a lateral direction extending to left and right sides of the human body; and
        a spacer configured to be arranged in the cavity of the main body and comprising a tool orienting slot for a tool to remove the spacer from the main body, wherein:
            at least one of the lid and the base defines an orienting slot arranged thereon, the orienting slot extending parallel to a front-rear direction and perpendicular to the spine direction and the lateral direction to establish an orientation reference for the spacer,
            the spacer is inserted in the cavity of the main body to fix the adjusted height of the cavity generated by the engagement between the receiving slot and the interconnect member, and
            the spacer has a height selected from a plurality of appropriate lengths to be equal to the adjusted height of the cavity for the main body to match the separation distance between the two adjacent spinous processes, and
    a stabilizing device for fixing the interspinous process device, the stabilizing device comprising:
        a pair of wing structures, each wing structure configured to extend along the longitudinal axis of the spine, each of the pair of wing structures comprising:
            a main body engaging portion located in a middle region of the wing structure, the main body engaging portion being configured to engage with the fixing member of the main body, wherein at least one of the pair of wing structures further comprises a fastener configured to be installed in a corresponding one of the main body engaging portions to fasten the main body and the stabilizing device together, and
            an end portion configured to abut against one of the two adjacent spinous processes.

2. The medical device according to claim 1, wherein the fastener in the at least one of the pair of wing structures includes at least two sub-fasteners that are structurally separable and both are installed in the corresponding one of the main body engaging portions.

3. The medical device according to claim 1, wherein the end portion comprises a plurality of spikes.

4. The medical device according to claim 3, wherein spikes in the plurality of spikes are arranged to form a staggered pattern.

5. The medical device according to claim 3, wherein a length of at least one of the plurality of spikes ranges from 0.5 mm to 22 mm.

6. The medical device according to claim 1, wherein at least one of the pair of wing structures comprises a groove to provide flexibility for the stabilizing device.

7. The medical device according to claim 1, wherein at least one of the pair of wing structures comprises one or more of a metal material, a plastic material, or a silicone material.

8. The medical device according to claim 1, wherein a length of at least one of the pair of wing structures ranges from 2 cm to 20 cm.

9. The medical device according to claim 1, wherein:
the corresponding one of the main body engaging portions further includes a through hole configured for engaging the main body with a corresponding one of the pair of wing structures by inserting the fixing member of the main body into the through hole,
the fastener is screwed into the corresponding one of the main body engaging portions to fix the inserted fixing member of the main body with the corresponding one of the main body engaging portions, and
a screwing direction of the fastener is substantially perpendicular to a direction of the through hole.

* * * * *